(12) United States Patent
Perkins et al.

(10) Patent No.: US 11,426,298 B2
(45) Date of Patent: Aug. 30, 2022

(54) APPARATUS AND METHODS FOR RESTORING TISSUE

(71) Applicant: Alucent Biomedical, Inc., Salt Lake City, UT (US)

(72) Inventors: D H Perkins, Salt Lake City, UT (US); RB Eugene Hayes, Salt Lake City, UT (US)

(73) Assignee: Alucent Biomedical, Inc., Salt Lake City, UT (US)

( * ) Notice: Subject to any disclaimer, the term of this patent is extended or adjusted under 35 U.S.C. 154(b) by 540 days.

(21) Appl. No.: 16/527,969

(22) Filed: Jul. 31, 2019

(65) Prior Publication Data
US 2021/0030573 A1    Feb. 4, 2021

(51) Int. Cl.
*A61F 2/958* (2013.01)
*A61M 25/10* (2013.01)
*A61F 2/82* (2013.01)
*A61F 2/24* (2006.01)

(52) U.S. Cl.
CPC ........... *A61F 2/958* (2013.01); *A61M 25/104* (2013.01); *A61M 25/1011* (2013.01); *A61F 2/2418* (2013.01); *A61F 2/82* (2013.01); *A61F 2002/9583* (2013.01); *A61M 2025/105* (2013.01); *A61M 2025/1013* (2013.01); *A61M 2025/1052* (2013.01)

(58) Field of Classification Search
CPC .. A61M 2025/1011; A61M 2025/1013; A61M 2025/1015; A61M 2025/1055; A61M 25/104; A61M 2025/105; A61M 25/006; A61F 2/945
See application file for complete search history.

(56) References Cited

U.S. PATENT DOCUMENTS

| 5,662,712 A * | 9/1997 | Pathak ................... B29C 70/74 606/195 |
| 5,899,917 A * | 5/1999 | Edwards ................ A61L 31/18 606/195 |
| 2009/0254064 A1* | 10/2009 | Boatman ............ A61M 25/1011 604/101.02 |
| 2014/0200504 A1* | 7/2014 | Rocha-Singh ..... A61B 17/2202 604/509 |

* cited by examiner

*Primary Examiner* — Bhisma Mehta
*Assistant Examiner* — John J Crawford
(74) *Attorney, Agent, or Firm* — Finnegan, Henderson, Farabow, Garrett & Dunner, LLP (57) ABSTRACT

An apparatus and methods tissue restoration are provided. The apparatus may include a catheter shaft extending from a proximal end to a distal tip and a translucent first distal balloon positioned on a translucent distal segment of the catheter shaft inside of and concentric with a second distal balloon proximal to the distal tip in fluid communication with a drug source via a first lumen, the first distal balloon may include first and second outer surfaces, and longitudinal and circumferential channels. A first light fiber and a second light fiber each positioned in the catheter shaft and extending through the translucent distal segment. The drug source provides at least one drug to the first distal balloon via the first lumen.

20 Claims, 9 Drawing Sheets

APPARATUS AND METHODS FOR RESTORING TISSUE

BACKGROUND

Technical Field

The present disclosure generally relates to apparatus and methods to restore a tissue's function. More particularly, and without limitation, the disclosed embodiments relate to catheters, and catheter systems to create a natural vessel scaffolding and restore tissue function.

Background Description

Balloon catheters are used in a number of surgical applications including occluding blood flow either distally or proximally of a treatment site. The inflation of the balloon must be controlled in order to avoid over-expansion or breakage of the balloon, which may rupture or otherwise damage the vessel. Percutaneous Transluminal Angioplasty (PTA), in which a balloon is used to open obstructed arteries, has been widely used to treat atherosclerotic lesions. However, this technique is limited by the vexing problems of re-occlusion and restenosis. Restenosis results from the excessive proliferation of smooth muscle cell (SMC), and the rate of restenosis is above 20%. Thus, about one in five patients treated with PTA must be treated again within several months.

Additionally, stenting is a popular treatment, in which a constricted arteriosclerotic segment of the artery is mechanically expanded with the aid of a balloon catheter, followed by placement of a metallic stent within the vascular lumen to restore the flow of blood. Constriction or occlusion of the artery is problematic and can be itself, or cause, a major health complications. Placement of a metallic stent has been found to result in the need for postoperative treatment in 20% to 30% of patients. One cause of this high frequency of required postoperative treatment is vascular intimal hyperplasia within the vascular lumen resulting in lumen narrowing despite the stent being placed. In order to decrease in-stent restenosis, attempts have been made to design a stent of a type having a surface carrying a restenosis-inhibiting drug so that when the stent is placed in an artery, the drug is eluted in a controlled manner within the vascular lumen. Those attempts have led to commercialization of drug-eluting stents (hereinafter referred to as DES) utilizing sirolimus (immunosuppressor) and paclitaxel (cytotoxic antineoplastic drug). However, since those drugs have an effect of inhibiting the proliferation of vascular cells (endothelial cells and smooth muscle cells) by acting on the cell cycle thereof, not only can the vascular intimal hyperplasia resulting from an excessive proliferation of the smooth muscle cells be suppressed, but proliferation is also suppressed of endothelial cells once denuded during placement of the stent. This can result in the adverse effect where the repair or treatment of the intima of a blood vessel becomes reduced. In view of the fact that thrombosis tends to occur more easily at a site less covered with endothelial cells in the intima of a blood vessel, an antithrombotic drug must be administrated for a prolonged time, say, half a year or so and, notwithstanding this antithrombotic drug administration, a risk of late thrombosis and restenosis will occur upon its discontinuance.

The technical problem addressed by the present disclosure is therefore to overcome these prior art difficulties by creating devices providing for controlled delivery of therapeutic agents to the surrounding tissues, propping the vessel open to a final shape, and functionalizing the therapeutic agent within the tissue and forming the cast shape, permitting blood flow and restoring tissue function. The solution to this technical problem is provided by the embodiments described herein and characterized in the claims.

SUMMARY

The embodiments of the present disclosure include catheters, catheter systems, and methods of forming a tissue scaffolding using catheter systems. Advantageously, the exemplary embodiments allow for controlled, uniform delivery of therapeutic agents to the surrounding tissues, casting the tissue to a final shape, and functionalizing the therapeutic agent in the tissue, forming the cast shape and propping the vessel open. The tissue may be a vessel wall of a vessel within the cardiovascular system.

According to embodiments of the present disclosure, an apparatus is provided. The apparatus may include a catheter shaft extending from a proximal end to a distal tip and a first distal balloon positioned on a translucent distal segment of the catheter shaft proximal to the distal tip and positioned inside of and concentric with a second distal balloon. The first distal balloon may be in fluid communication with a drug source via a first lumen. The first distal balloon may include a translucent material, a plurality of longitudinal channels recessed from a plurality of outermost radial surfaces of the first distal balloon, and a plurality of circumferential channels recessed from the outermost radial surfaces of the first distal balloon. The apparatus may include a second distal balloon in fluid communication with a second lumen separate from the first lumen, and a first light fiber and a second light fiber each positioned in the catheter shaft and extending through the translucent distal segment.

In some embodiments, the second distal balloon includes a plurality of slitted apertures radially aligned with the outermost radial surfaces of the first distal balloon, the slitted apertures selectively communicate the drug from the first distal balloon to a treatment area of a subject. The slitted apertures may be positioned away from the longitudinal channels and the circumferential channels of the first distal balloon. The slitted apertures of the second distal balloon may remain in contact with the outermost radial surfaces of the first distal balloon, sealing the slitted apertures closed during inflation and deflation of the first distal balloon. During inflation of the second distal balloon, the fluid fills between an inside surface of the second distal balloon and an outside surface of the first distal balloon, gradually filling the longitudinal channels and circumferential channels. A pressure of the fluid between the inside surface of the second distal balloon and the outside surface of the first distal balloon increases and inflates the second distal balloon, the increased pressure forces edges of the slitted aperture to open apart thereby reducing the pressure. Inflation of the second distal balloon moves the slitted apertures away from the outermost radial surfaces of the first distal balloon allowing the slitted apertures to open and permit fluid flow to the treatment area.

In some embodiments, the translucent material of the distal segment, the first distal balloon, and the second distal balloon is transparent. The first light fiber and the second light fiber may provide light activation through the distal segment, the first distal balloon, and the second distal balloon. The longitudinal channels and circumferential channels are non-deformable and provide uniform drug delivery through the second distal balloon. The second distal balloon may include material that conforms to the morphology of the vessel wall.

Embodiments of the present disclosure also provide a method of tissue restoration in a blood vessel of a subject. The method may include providing a catheter into the blood vessel. The catheter may include a catheter shaft extending from a proximal end to a distal tip and a first distal balloon positioned on a translucent distal segment of the catheter shaft proximal to the distal tip and positioned inside of and concentric with a second distal balloon. The first distal balloon may be in fluid communication with a drug source via a first lumen. The first distal balloon may include a translucent material, a plurality of longitudinal channels recessed from a plurality of outermost radial surfaces of the first distal balloon, and a plurality of circumferential channels recessed from the outermost radial surfaces of the first distal balloon. The apparatus may include a second distal balloon in fluid communication with a second lumen separate from the first lumen, and a first light fiber and a second light fiber each positioned in the catheter shaft and extending through the translucent distal segment. The method may include supplying a drug from the drug source to the first distal balloon, delivering the drug to the treatment area through the slitted apertures, and activating the first light fiber and the second light fiber thereby providing light transmission through the distal segment, the first distal balloon, and the second distal balloon to activate the drug in the treatment area.

The method may further include gradually filling the drug into a volume of the longitudinal channels and circumferential channels between an inside surface of the second distal balloon and an outside surface of the first distal balloon, and expanding the second distal balloon, thereby moving the slitted apertures away from the outermost radial surfaces of the first distal balloon. The method may further include contracting the second distal balloon as fluid is delivered through the slitted apertures. Contracting the second distal balloon may move the second distal balloon into contact with the outermost radial surfaces of the first distal balloon and closes the slitted apertures, causing drug delivery to stop.

Embodiments of the present disclosure also provide an apparatus including a catheter shaft extending from a proximal end to a distal tip and a first distal balloon positioned on a translucent distal segment of the catheter shaft proximal to the distal tip and positioned inside of and concentric with a second distal balloon. The first distal balloon may be in fluid communication with a drug source via a first lumen. The first distal balloon may include a translucent material, a plurality of longitudinal channels recessed from a plurality of outermost radial surfaces of the first distal balloon, and a plurality of circumferential channels recessed from the outermost radial surfaces of the first distal balloon. The apparatus may include a second distal balloon in fluid communication with a second lumen separate from the first lumen, and a first light fiber and a second light fiber each positioned in the catheter shaft and extending through the translucent distal segment. The drug source is configured to provide at least one drug to the first distal balloon via the first lumen and during inflation of the second distal balloon, the fluid fills between an inside surface of the second distal balloon and an outside surface of the first distal balloon, gradually fills the longitudinal channels and circumferential channels.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

DETAILED DESCRIPTION

Reference will now be made in detail to embodiments and aspects of the present disclosure, examples of which are illustrated in the accompanying drawings. Where possible, the same reference numbers will be used throughout the drawings to refer to the same or like parts.

Figure 1:
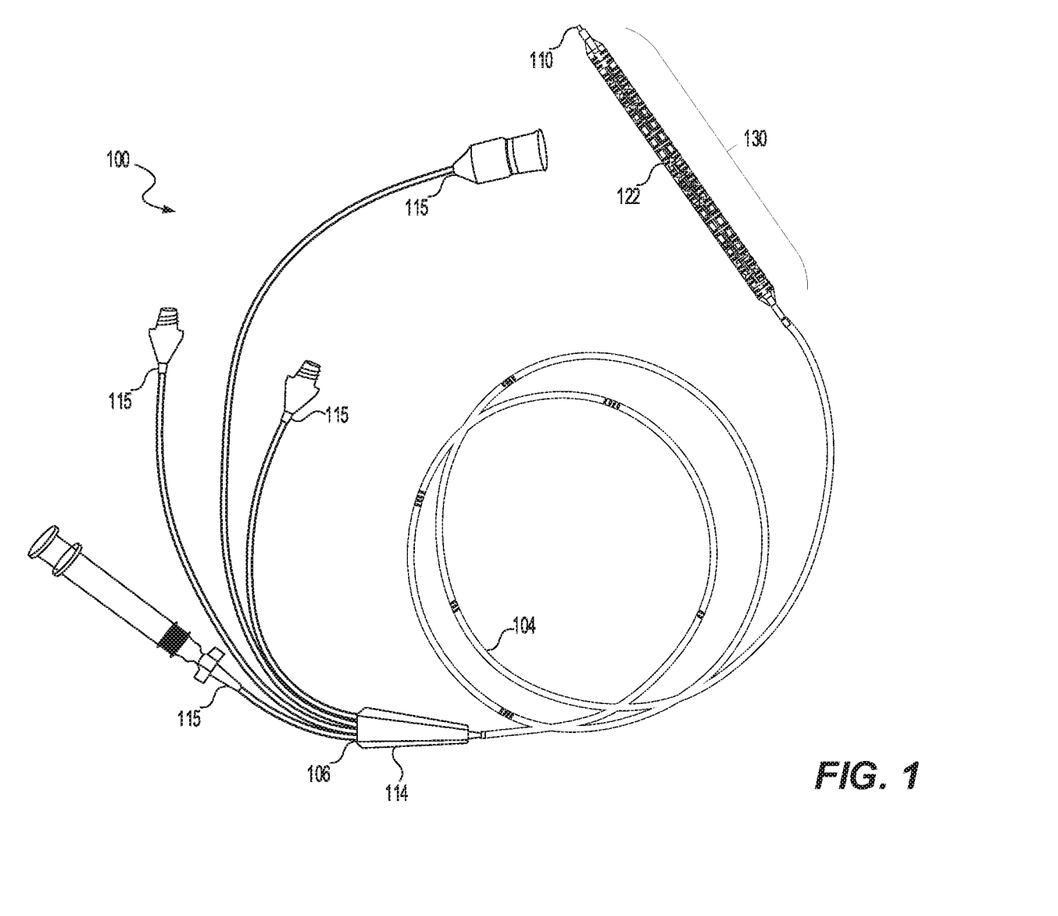
FIG. 1 is a side elevational view of an exemplary apparatus including a catheter, according to embodiments of the present disclosure.

FIG. 1 illustrates an apparatus 100 in accordance with an embodiment of this disclosure. The apparatus 100 having a catheter shaft 104 that extends from a proximal end 106 to a distal tip 110 of the apparatus 100. The apparatus 100 may be configured for longitudinal movement and positioning within a vessel (e.g. blood vessel) of a subject. In some embodiments, the apparatus 100 may be configured for treatment of an area of the vessel. In some embodiments, the apparatus 100 may occlude the vessel, while in other embodiments the apparatus may not occlude the vessel. For example, the apparatus 100 may be configured for delivery of a drug to an area of the vessel occupied by the apparatus 100 which may form and cast a shape in the vessel, as will be described in more detail below.

The apparatus 100 may include a proximal end connector 114 positioned at the proximal end of the apparatus 100, and the catheter shaft 104 may extend in a distal direction therefrom. The catheter shaft 104 may define a plurality of lumens that are accessible via a plurality of ports the proximal end connector 114. The plurality of ports 115 may be configured to engage with external sources desirable to communicate with the plurality of lumens. The ports may engage with external sources via a variety of connection mechanisms, including, but not limited to, syringes, overmolding, quick-disconnect connectors, latched connections, barbed connections, keyed connectors, threaded connections, or any other suitable mechanism for connecting one of the plurality of ports to an external source. Non-limiting examples of external sources may include inflation sources (e.g. saline solutions), gaseous sources, treatment sources (e.g. medication, drugs, or any desirable treatment agents discussed further below), light sources, among others. In some embodiments, apparatus 100 can be used with a guide wire (not shown), via guide wire lumen 164 (see FIG. 5A), to assist in guiding the catheter shaft 104 to the target area of the vessel.

Figure 2:
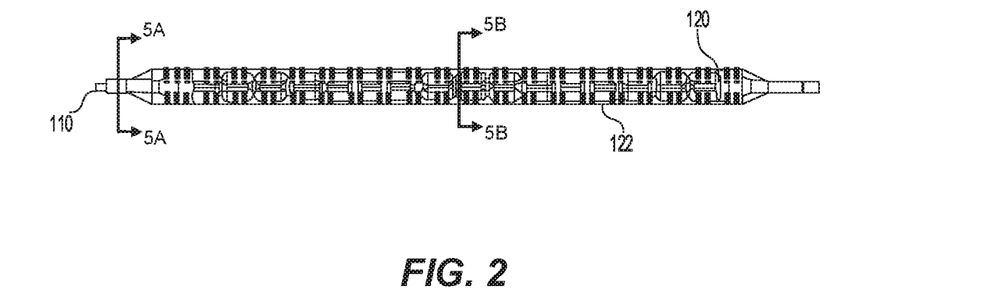
FIG. 2 is a side elevational view of a distal portion of the catheter of FIG.
Figure 3:
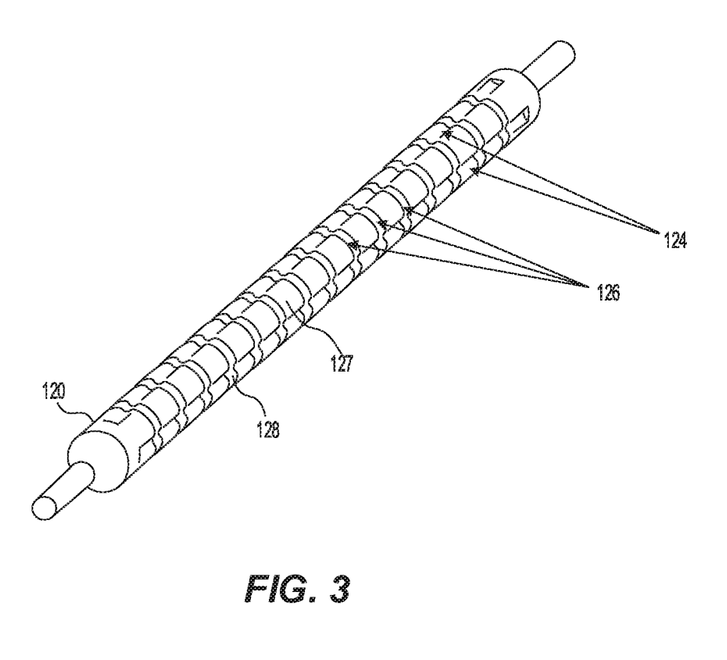
FIG. 3 is a perspective view of an exemplary first balloon of the exemplary catheter of FIG. 1.

FIGS. 1, 2, and 3 illustrate the apparatus 100 may include a first distal balloon 120 positioned inside of and concentric with a second distal balloon 122 over a distal segment 130 of the catheter shaft 104 proximal to the distal tip 110. In some embodiments, the first distal balloon 120 may be proximally offset from the distal tip 110 a distance between 0 mm and 1 mm, 0 mm and 2 mm, 0 mm and 3 mm, 0 mm and 10 mm, or 0 and 50 mm. The first distal balloon 120 may take any shape suitable for supporting a wall of a blood vessel or other hollow body structure of the subject when the compliant or semi-compliant balloon is inflated.

The second distal balloon 122 may have one continuous surface sealed at each end around the catheter shaft 104 forming an enclosed volume and in fluid communication through a port with the catheter shaft 104 through a distinct and separate lumen from the first distal balloon 120. The second distal balloon 122 may be substantially translucent. In some embodiments, the second distal balloon 122 may inflate to 2 to 10 millimeters (mm) in diameter. In other embodiments, the second distal balloon 122 may inflate to 1 to 8 cm in diameter. The second distal balloon 122 may have a length of about 0.5 to 1 centimeters (cm), 1 to 2 cm, 1 to 3 cm, or 1 to 5 cm, or 1 to 10 cm, or 1 to 15 cm, or 1 to 20 cm, or 1 to 25 cm, and may take any shape suitable for supporting a wall of a blood vessel of the subject when the non-compliant or semi-compliant balloon is inflated. For example, the second distal balloon 122 may expand into a cylindrical shape surrounding the distal segment 130 of the catheter shaft 104. The cylindrical shape may be gradually tapered inward at a proximal end and a distal end of the second distal balloon 122, thereby providing a gradually tapered proximal end and distal end of the second distal balloon 122 that taper into contact with and become flush with the catheter shaft 104.

Non-limiting examples of shapes the inflated second distal balloon 122 may form include a cylindrical shape, football-shaped, spherical, ellipsoidal, or may be selectively deformable in symmetric or asymmetric shapes so as to limit the potential difference in the treated vessel shape and the untreated vessel shape reducing edge effects common between two surfaces of different stiffness as found in metal stents. The force exerted against a vessel interior by second distal balloon 122 may be strong enough to scaffold the vessel wall with the apparatus 100 held in a stationary position within the vessel or other hollow body structure. However, the force is not so great as to damage the interior surface of the vessel or other hollow body structure.

The apparatus 100 may include a plurality of connectors 115 positioned proximally to the proximal end connector 114. For example, the first distal balloon 120 may be terminated at the proximal end with a connector capable of receiving a drug source. In some embodiments, the connector may be a luer configuration. The second distal balloon 122 may be terminated at the proximal end with a separate and distinct connector capable of receiving a fluid for inflation, which may, in some embodiments, be a luer configuration. A center lumen (discussed in more detail below), may be terminated at the proximal end with a connector capable of receiving a fluid source for clearing the lumen from the proximal termination to outside the distal tip, and in some embodiments may include a luer configuration. The center lumen may also accommodate a guidewire for tracking the catheter apparatus to the desired anatomical location. As discussed in more detail below, the apparatus 100 may also include light fibers that may be terminated at the proximal end with an adaptor capable of connecting with a light source. Each light fiber may terminate with a separate and distinct adaptor or each light fiber may share an adaptor to a light source.

The materials of the apparatus 100 may be biocompatible. The catheter shaft 104 may include material that is extrudable and capable of sustaining lumen integrity. The distal segment 130 of the catheter shaft 104 is substantially translucent to allow light transmission from light fibers. The catheter shaft 104 material is rigid enough to track over a guidewire and soft enough to be atraumatic. The catheter shaft 104 may be made of materials including, but not limited to polymers, natural or synthetic rubber, metal and plastic or combinations thereof, nylon, polyether block amide (PEBA), nylon/PEBA blend, thermoplastic copolyester (TPC), a non-limiting example may be HYTREL® (available from Dupont de Nemours, Inc. of Wilmington, Deleware), and polyethylene. The shaft materials can be selected so as to maximize column strength to the longitudinal length of the shaft. Further, the shaft materials can be braided, so as to provide sufficient column strength. The shaft materials can also be selected so as to allow the device to move smoothly along a guide wire. The catheter shaft 104 can also be provided with a lubricious coating as well as antimicrobial and antithrombogenic coatings. The shaft materials should be selected so as not to interfere with the efficacy of the agent to be delivered or collected. This interference may take the form of absorbing the agent, adhering to the agent or altering the agent in any way. The catheter shaft 104 of the present disclosure may be between about 2-16 French units ("Fr." where one French equals ⅓ of a millimeter, or about 0.013 inches). The catheter shafts to be used in coronary arteries may be between about 3-5 Fr. in diameter, and more specifically may be 3 Fr. The catheter shafts to be used in peripheral vessels may be between about 5-8 Fr. in diameter, and more specifically 5 Fr. The catheter shafts to be used in the aorta may be between about 8-16 Fr. in diameter, and more specifically 12 Fr.

The first distal balloon 120 and the second distal balloon 122 may be substantially translucent permitting light from light fibers to be transmitted substantially beyond the inflated diameters of the second distal balloon 122. The second distal balloon 122 may be compliant such that the material conforms substantially to a vessel's morphology. The first distal balloon 120 material may be more rigid and noncompliant, capable of higher internal pressures with minimal outward expansion for opening vessels that are more resistant to pressures. The compliance of the first distal balloon and second distal balloon may be comparable or dissimilar. For example, the first distal balloon 120 may be non-compliant, capable of higher internal pressures with minimal outward expansion for propping open and casting a vessel into optimal shapes. The second balloon 122 material may be elastic, capable of covering the first distal balloon 120 as a skin or covering, expanding and contracting with the inflation of the first distal balloon 120 and elastically conforming substantially to a vessel's morphology for optimal drug delivery. The second distal balloon 122 may include material that conforms to the morphology of the vessel wall thereby providing optimal drug delivery in a non-dilating and non-traumatic manner. The apparatus 100 may not cause any further trauma (e.g. trauma caused by atherectomy or percutaneous transluminal angioplasty "PTA" or vessel preparation methods) to the vessel to promote optimal healing.

The balloons may be thick or thin for performance optimization. The first distal balloon 120 may be thicker (0.002 inches) to better form the fluid channels and prop the vessel wall for shaping. The second distal balloon may be thicker (0.002 inches) to better form the opening and closing function of the perforations 198 described in more detail below.

FIG. 3 is a perspective view of the first distal balloon 120 with the surrounding second distal balloon 122 removed. In some embodiments, the first distal balloon 120 may not be a percutaneous transluminal angioplasty balloon or a high-pressure apparatus, but instead the first distal balloon 120 may be non-dilating and used for vessel shape forming or propping a vessel open. The first distal balloon 120 includes a plurality of longitudinal fluid channels 124 and a plurality of circumferential fluid channels 126. The longitudinal fluid channels 124 extend along the length of the first distal balloon 120, each longitudinal fluid channel 124 being spaced apart from other longitudinal fluid channels 124 and each longitudinal fluid channel 124 intersecting with a plurality of circumferential fluid channels 126 along the length of the first distal balloon 120. The longitudinal fluid channels 124 and the circumferential channels 126 may intersect at an angle from 10° to 170°. The circumferential fluid channels 126 extend around the circumference of the first distal balloon 120, each circumferential fluid channel 126 being spaced apart from other circumferential fluid channels 126. The longitudinal fluid channels 124 and the circumferential fluid channels 126 each having a depth, where the depth of the fluid channels is measured in relation to an outer surface 127 of the first distal balloon 120. Accordingly, the longitudinal fluid channels 124 and the circumferential fluid channels 126 are recessed from the outer surface 127 of the first distal balloon 120. The depth of the longitudinal fluid channels 124 and the circumferential fluid channels 126 may be the same depth or different depths. The longitudinal fluid channels 124 and the circumferential fluid channels 126 may be non-deformable. In some embodiments, the fluid channels 124, 126 promote the first distal balloon 120 to fold.

Figure 4:
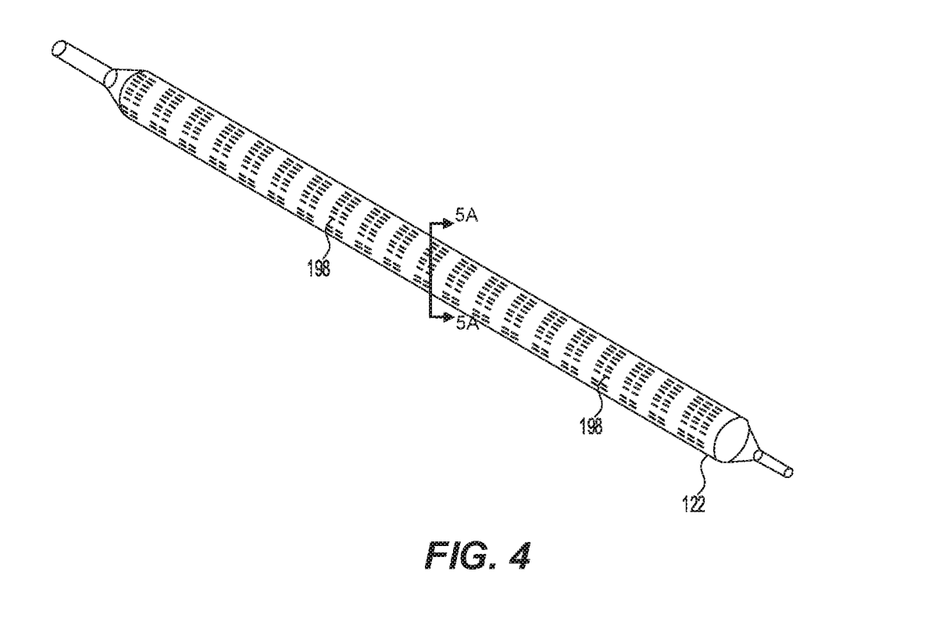
FIG. 4 is a perspective view of an exemplary second balloon of the exemplary catheter of FIG. 1.

FIG. 4 illustrates the second distal balloon 122 that may include material that is substantially translucent and elastic, capable of remaining in contact with the outermost radial surface of the first distal balloon 120, and may act as a covering or skin of the first distal balloon 120, during inflation and deflation of the first distal balloon 120. The second distal balloon 122 may include a plurality of perforations 198 penetrating through the balloon wall. The perforations 198 may be slitted apertures. The slitted apertures 198 may be in fluid communication from the inside surface of the second distal balloon 122 to the outside surface of the second distal balloon 122, as described in more detail below. The perforations 198 may be formed in an inflated or expanded material state whereupon in a deflated or contracted state the perforations remain naturally closed.

Figure 5A:
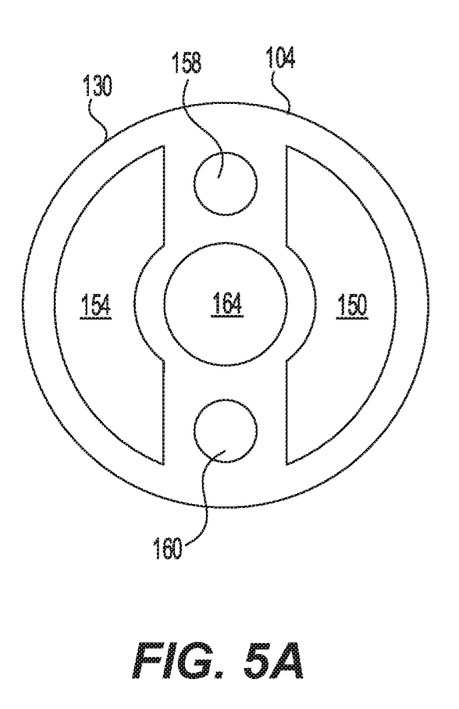
FIG. 5A is a cross-sectional view taken along line 5A-5A of FIG. 2.

FIG. 5A is a cross-sectional view taken along line 5A-5A of FIG. 2 showing a plurality of lumens within the assembly 100, according to an embodiment of this disclosure. The catheter shaft 104 may have an outside diameter and outside surface 130. The catheter shaft 104 may have an inside configuration of five distinct and separate lumens, extending from the proximal end 106 to the distal tip 110.

The first distal balloon 120 may be in fluid communication with a first distal balloon inflation lumen 150. The second distal balloon 122 may be in fluid communication with a second distal balloon inflation lumen 154 that is separate and distinct from the first distal balloon inflation lumen 150. The first distal balloon 120 may be in fluid communication with an inflation source via the first distal balloon inflation lumen 150 separate from the second distal balloon inflation lumen 154. The first distal balloon inflation lumen 150 may extend through the catheter shaft 104 and have an input at one of the plurality of ports 115 of the proximal end connector 114. Fluid communication between the first distal balloon 120 and the inflation source via the first distal balloon inflation lumen 150 may cause the first distal balloon 120 to selectively fill separately from and independently of the second distal balloon 122. Similarly, the second distal balloon 122 may be in fluid communication with an inflation source via the second distal balloon inflation lumen 154 separate from the first distal balloon inflation lumen 150. Fluid communication between the second distal balloon 122 and the inflation source via the second distal balloon inflation lumen 154 may cause the second distal balloon 122 to selectively inflate and deflate separately from and independently of the first distal balloon 120.

A first light fiber lumen 158 and a second light fiber lumen 160 may be positioned in the catheter shaft 104 to receive light fibers, and the first light fiber lumen 158 and the second light fiber lumen 160 may extend from the proximal end 106 into the distal segment 130, and may be positioned substantially symmetric, longitudinally opposed and parallel one to another within the catheter shaft 104. In another exemplary embodiment, the catheter shaft 104 may include a single light fiber lumen. In still other embodiments, the catheter shaft 104 may include a plurality of light fiber lumens.

A guidewire lumen 164 may be concentric with the catheter shaft outside diameter and may be arranged in the catheter shaft 104, from the proximal end 106 through the distal tip 110. The guidewire lumen 164 may accommodate a guidewire to aid the placement of the apparatus 100 to a desired anatomical position communicating with the proximal end and distal tip. The guidewire may be separate and distinct from the apparatus 100 and extend proximally beyond the proximal end and distally beyond the distal tip of the catheter shaft. The guidewire lumen 164 is located concentric with the catheter outer diameter; the catheter shaft is oriented concentrically with the guidewire permitting the catheter shaft 104 to follow the guidewire without favoring one side of the catheter shaft 104 or whipping from side to side. The guidewire may remain in the guidewire lumen 104 maintaining anatomical position during the activation of the light fibers.

Figure 5B:
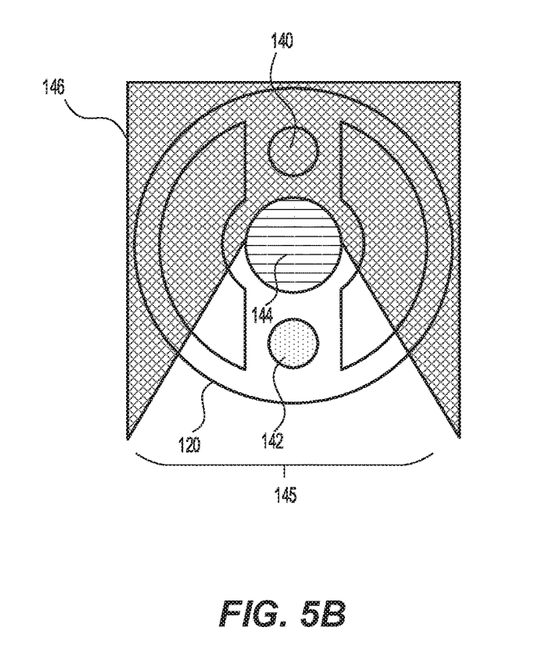
FIGS. 5B and 5C are cross-sectional views taken along line 5B-5B of FIG. 2A, removing portions of the external structure.
Figure 5C:
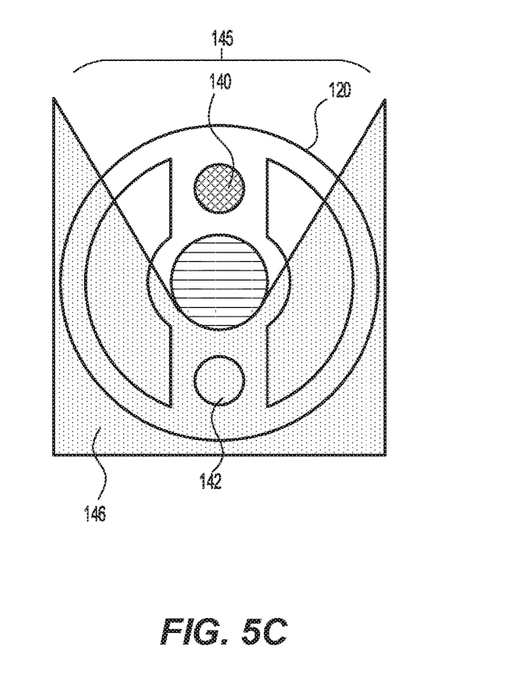

FIGS. 5B and 5C illustrate cross-sectional views taken along line 5B-5B of FIG. 2. The apparatus 100 may further include a first light fiber 140 and a second light fiber 142 positioned in the catheter shaft 104 and extending through the distal segment 130. The light fibers 140, 142 may transmit light through the distal segment 130, the second distal balloon 122, the first distal balloon 120. The light fiber 140 may be connected to the proximal end connector 114 and may have proximal ends that connect to a light fiber activation source via at least one of the plurality of ports 115. In some embodiments, the light fibers 140, 142 may be configured to transmit light at a wavelength of 375 nanometers (nm) to 475 nm, and more specifically 450 nm that transmits through the distal segment 130 and the first distal balloon 120. The light fibers 140, 142 may emit light outside of the ultraviolet (UV) range of 10 nm to 400 nm. In some embodiments, the light first fiber 140 may be positioned in the first light fiber lumen 158 and the second light fiber 142 may be positioned in the second light fiber lumen 160.

In some embodiments, light from the light fibers 140, 142 may be unable to penetrate through a guidewire 144 forming a shadow 145 opposite the light and beyond the guidewire 144. Accordingly, the light fibers 140, 142 may each generate a respective light transmission area 146. The light fiber lumens 158, 160 are oriented substantially opposite one another minimizing the shadow 145 formed by the light impenetrable guidewire 144, permitting the transmission of light to penetrate the circumference of the catheter shaft 104 from the first light fiber 140 or the second light fiber 142. In another embodiment, the catheter shaft 140 may include a single light fiber, and the guidewire may be removed for light penetration to the outer tissue.

In some embodiments, the light fibers 140, 142 may be made from plastic core and cladding. The refractive index of the core is high. The refractive index of the cladding is low. A non-limiting example of the core material may be polymethyl methacrylate (PMMA). A non-limiting example of the cladding may be a silicone material. The light source may control the wavelength and supplied power of the light fibers 140, 142. The pattern of the breaks in the cladding of the light fiber ensure uniform power distribution to the vessel wall. Longer lengths have a different pattern than shorter lengths. The distal lengths of cladding breaks are matched to the length of the balloons.

Figure 6:
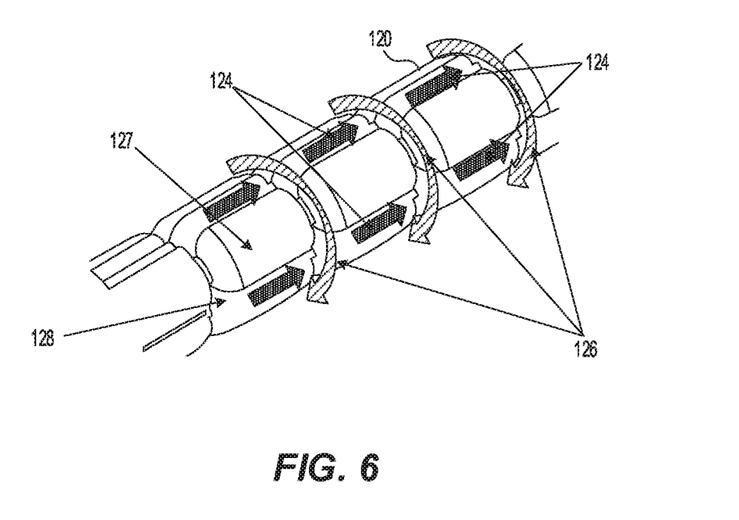
FIG. 6 is a perspective detailed view of the first balloon of FIG. 3.

As illustrated in FIGS. 3 and 6, the longitudinal fluid channels 124 and circumferential fluid channels 126 may form a pattern that may be interconnected. The interconnected longitudinal fluid channels 124 and circumferential fluid channels 126 of the pattern generate a volume that fluid may fill in the channels. The longitudinal fluid channels 124 and circumferential fluid channels 126 form outermost radial surfaces (e.g. outer surface 127) and innermost radial surfaces (e.g. inner surface 128). The outermost radial surfaces 127 may contact the vessel wall and may shape or cast the vessel, propping it open without overstretching or substantially dilating the vessel wall.

As shown in FIG. 6, the innermost radial surfaces 128 permit fluid to flow longitudinally and circumferentially, following the directional arrows, supplying fluid throughout the entire innermost surface 128 of the first distal balloon 120 for subsequent uniform delivery through the second distal balloon 122, as described below. The longitudinal channels 124 facilitate longitudinal fluid flow along the flow direction arrows, and the circumferential channels 126 facilitate circumferential fluid flow along the flow direction arrows. The number of fluid channels (e.g. longitudinal channels 124 and circumferential channels 126), outermost radial surfaces 127, and innermost radial surfaces 128 may vary to optimize delivery function and remain shaped and functional during the entire inflation pressure range for continuous fluid supply. In some embodiments, the longitudinal fluid channels 124 may permit a preferential material weakness for folding the balloon.

Figure 7:
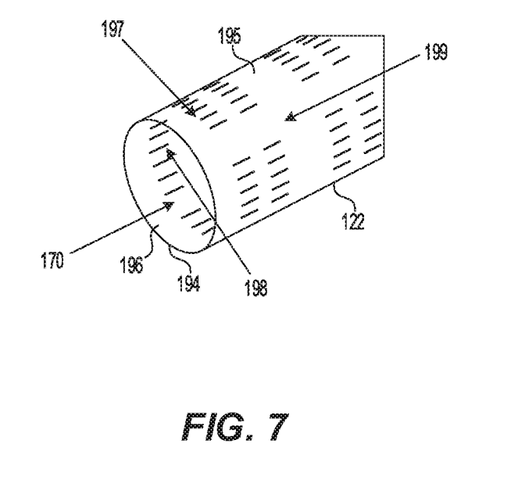
FIG. 7 is a perspective cross-sectional view from line 6-6 of FIG. 4, removing portions of the internal structure.

FIG. 7 illustrates the second distal balloon 122 may have a thickness 194 forming an outside surface 195 and an inside surface 196. The inside surface 196 forms a confined and isolated volume 170 in fluid communication with the proximal end 106 of the catheter shaft 104 and a plurality of slitted apertures 198. The second distal balloon 122 may include material that is substantially translucent and elastic, capable of remaining in contact with the outermost radial surface 127 of the first distal balloon 120, acting as a covering or skin, during inflation and deflation of the second distal balloon 122. The second distal balloon 122 may include material that is a porous membrane (ePTFE) substantially non-translucent and elastic, capable of permitting substantial light transmittance, and capable of remaining in contact with the outermost radial surface 127 of the first distal balloon 120, acting as a covering or skin, during inflation and deflation of the second distal balloon 122. The second distal balloon 122 may include a plurality of slitted apertures 198 which may be perforations that penetrate through thickness 194 of the wall of the second distal balloon 122 in fluid communication from the inside surface 196 of the balloon 122 to the outside surface 195 of the balloon 122.

Slitted apertures 198 may be arranged in a circumferential and/or longitudinal pattern. The slitted apertures 198 in regions 197 that are radially aligned with the outermost radial surfaces 127 of the first distal balloon 120 and the catheter shaft 104, and substantially absent in regions 199 aligned with the innermost radial surfaces 128 where the longitudinal fluid channels 124 and circumferential fluid channels 126 are positioned. "Substantially absent" may refer to the slitted apertures being positioned away from the first distal balloon regions of innermost radial surfaces 128 where the longitudinal fluid channels 124 and circumferential fluid channels 126 are positioned. This pattern permits the slitted apertures 198 of the second distal balloon 122 to remain in contact with the outermost radial surfaces 127 of the first distal balloon 120, sealing the slitted apertures 198 closed during the inflation and deflation of the first distal balloon 120. The slitted apertures 198 may only open and permit fluid flow upon subsequent inflation of the second distal balloon 122, inflation of the second distal balloon 122 lifts the slitted apertures 198 away from the outermost radial surfaces 127 of the first distal balloon 120. The inflation of the second distal balloon 122 moving the slitted apertures 198 away from the outermost radial surfaces 127 allows the slitted apertures 198 to function as microvalves and selectively deliver fluid to the vessel wall. The second distal balloon 122 may include at least one slitted aperture 198 with a maximum length substantially the same as the length of the outermost surface 195 (i.e., eight outermost surfaces 195, eight slitted apertures 198 the length of the outermost surface 195). The number and length of the slitted apertures 198 may vary to accommodate the desired function; however, the pattern must be followed for proper operation, ensuring the absence of slitted apertures 198 near the longitudinal fluid channels 124 and circumferential fluid channels 126 of the first distal balloon 120.

FIGS. 8A-8F illustrate an inflation sequence in accordance with embodiments of the present disclosure. Although the second distal balloon 122 is not specifically shown in FIGS. 8A-8F, the second distal balloon 122 is expanded by the fluid pressure generated by the fluid patterns shown in FIGS. 8E and 8F.

Figure 8A:
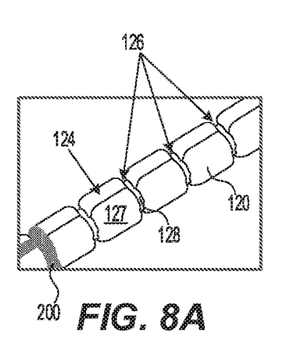
FIGS. 8A-8F show a series of internal perspective views illustrating a filling sequence in accordance with embodiments of the present disclosure.
Figure 8B:
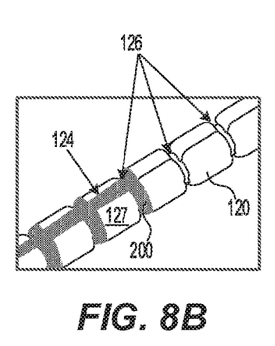
Figure 8C:
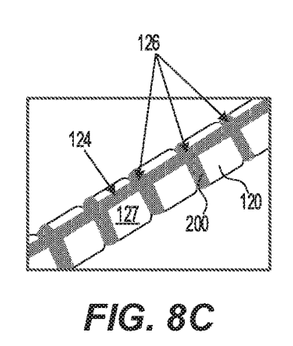
Figure 8D:
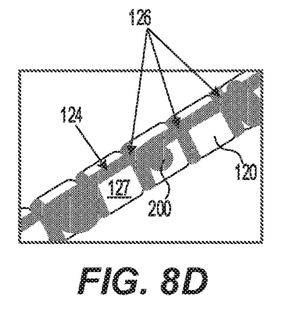
Figure 8E:
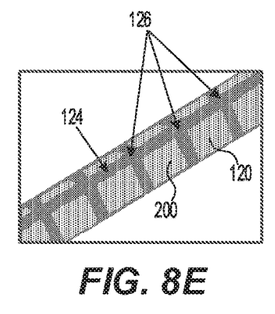
Figure 8F:
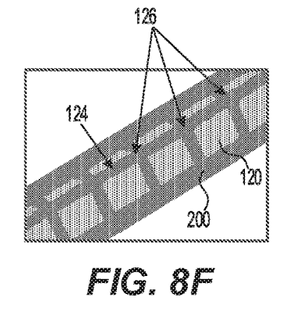

Inflating the first distal balloon 120 forms a substantially invariable fluid channel structure covered by the second distal balloon 122 which may be elastic. As illustrated in FIGS. 8A-8C, the fluid 200 fills longitudinal fluid channels 124 and circumferential fluid channels 126 first, the fluid 200 filling between the innermost surface 128 and the outermost surface 127 of the first distal balloon 120 and the internal surface 196 of the second distal balloon 122, away from the slitted apertures 198 which are aligned with and contacting the outermost surfaces 127 of the first distal balloon 120. Fluid pressure builds in the volume between the innermost surface 128 and the outermost surface 127 of the first distal balloon 120 and the internal surface 196 of the second distal balloon 122, which causes the elastic second distal balloon 122 to begin to move away from the outermost surfaces 127 of the first distal balloon 120, allowing fluid 200 to begin to flow onto the outermost surfaces 127, as shown in FIG. 8D. As pressure continues to build, the second distal balloon 122 continues to expand, allowing fluid 200 to flow uniformly around the outer surfaces 127 and fluid channels of the first distal balloon 120 (FIG. 8E), until the second distal balloon 122 is fully expanded and fluid 200 begins flowing through the slitted apertures 198 (after FIG. 8F is achieved).

The fluid 200 may be a drug source and provide a therapeutic purpose when functionalized with a light source at the proper wavelength. Following the path of least resistance, the inflation fluid 200 of the second distal balloon 122 will fill the circumferential channels 126 and longitudinal fluid channels 124 of the first distal balloon 120. Absent slitted apertures 198 in the second distal balloon 122, in regions of the first distal balloon 120 innermost radial surfaces 128 or fluid channels (e.g. 124, 126), the innermost radial surfaces 128 or fluid channels 124 or 126 of the first distal balloon 120 will substantially fill with fluid 200. The slitted apertures 198 of the second distal balloon 122 remain in contact with the outermost radial surface 127 of the first distal balloon 120, sealed and closed. Once the first distal balloon fluid channels 124, 126 are filled, further inflation of the second distal balloon 122 will cause the material to expand, lifting the slitted apertures 198 away from the first distal balloon outermost surfaces 127, opening and unsealing the slitted apertures 198 and permitting fluid 200 to flow through the slitted apertures 198. Once inflation has stopped, the fluid 200 will exit from the unsealed slitted apertures 198 until only the fluid channels 124, 126 of the first distal balloon are filled, permitting the inner surface 196 of the second distal balloon 122 to rest on the outermost radial surfaces 127 of the first distal balloon 120, once again closing and sealing the slitted apertures 198. In this manner, inflating and deflating the second distal balloon 122 may selectively control the delivery of the drug source, acting as a series of microvalves in "on" and "off" conditions. Similarly, the second distal balloon 122 may be a porous membrane material with small pores under low pressure and larger pores under higher pressure. The first distal balloon 120 operates and performs as described. The second distal balloon 122 operates and performs as described, filling fluid channels 124 and 126 before contacting the inner surface 196; except, the pores of the second distal balloon 122 remain closed until the pressure builds enough to open the pores and permit the drug to flow from the outer surface of the first distal balloon 120 to the outer surface of the second distal balloon 122, acting as a series of microvalves in "open" and "closed" conditions The target area for a delivery of drug source may be a vessel of the cardiovascular system. The target area may be first prepared by percutaneous transluminal angioplasty (PTA) or atherectomy to displace or remove damaged vessel cellular debris. The catheter apparatus 100 is not intended to replace PTA; the functional pressure of the first distal balloon 120 is only sufficient to prop open the vessel during drug functionalization. The first distal balloon 120 may be inflated, forming fluid channels (e.g. 124, 126); the outermost radial surfaces 127 contacting the inner surface 196 of the second distal balloon 122. The second distal balloon 122 is inflated with a drug source, the fluid channels 124, 126 of the first distal balloon 120 fill first, followed by the lifting of the slitted apertures 198 off of the first distal balloon outermost radial surfaces 127, which uniformly delivers the drug source to the vessel wall.

In the event slitted apertures 198 are positioned near a smaller vessel, side branch or collateral, only the drug from those slitted apertures 198 will be lost to the smaller vessels. However, all the remaining slitted apertures 198 will deliver drug to their adjacent vessel walls such that drug is delivered uniformly to the vessel wall with minimal loss to other areas. In some embodiments, while the first distal balloon 120 is inflated, propping open the vessel wall and shaping the vessel diameter, the light source may be activated during or after drug delivery.

The edges of the slitted apertures 198 may remain together and closed the first distal balloon 120 and second distal balloon 122 are filled with a drug source, allowing the first distal balloon 120 and second distal balloon 122 to nearly fill and inflate without loss of the drug source. As the second distal balloon 122 volume fills and inflates, the pressure will increase, forcing the edges of the slitted aperture 198 to open and allow the fluid to exit through the slitted apertures 198, reducing the balloon pressure. Similarly, as the volume and corresponding pressure of the second distal balloon 122 is reduced from fluid flowing out through the slitted apertures 198, the edges of the slitted aperture 198 may close together and may stop fluid flow through the slitted apertures 198 when they come into contact with the outer surfaces 127 of the first distal balloon 120. In this manner of inflating and deflating the first distal balloon 120 and the second distal balloon 122 may control the delivery of the drug source as the slitted apertures 198 are opened and closed.

In some embodiments, the apparatus 100 may be capable of delivering two drugs simultaneously. For example, the outside of the second distal balloon 122 may be coated with a first drug and a second drug may be delivered through the slitted apertures 198. Accordingly, the first drug and the second drug may be different drugs. In some embodiments, the first drug and the second drug may be the same drug. In a non-limiting example, the second distal balloon 122 inner or outer surface may be coated with Paclitaxel and infusing an aqueous drug or saline through the slits to the vessel wall.

While in this vessel supported position, a light source may be supplied to the light fibers 140, 142 in the catheter shaft 104 for transmittance through the catheter shaft 104, through the first distal balloon 120 and the second distal balloon 122, and into the vessel wall 182 as previously described.

There are several combinations for the local delivery of a drug source. For example, a solid drug may be coated on the outside surface of the second distal balloon 122 and an aqueous drug may be delivered through the slitted apertures 198 of the second distal balloon 122. The drug may be the same, one solid and one aqueous, each penetrating the vessel wall differently. The drugs may be complimentary, but different substances (e.g., one drug may cross-link collagen restoring vessel properties and a complimentary drug may be an antiproliferative reducing procedure related inflammation). The aqueous or solid drug may assist in the capacity of an excipient or activate its counterpart through a controlled reaction. The drugs may be dissimilar and non-complimentary affecting the vessel wall through substantially different methods of action. The drugs may be delivered by the same apparatus (e.g. 100) in sequence, one after the other, or with a timed delay, or multiple times at the same location or at subsequent locations multiple times, permitting the most effective treatment procedure. The drugs may be functionalized with the light source simultaneously with the delivery (i.e., the light source remains on during the delivery of the drug through the slitted apertures 198). The drugs may be effective when the drugs are near tissue components and functionalized by a light source.

In some embodiments, the drug is not cured or activated, but the drug is functionalized to cross-link with tissue proteins. The tissue proteins, the drug, and the light may be present to create a therapeutic effect. The functionalizing of the drug may not be time dependent, but instantaneous, dependent on wavelength alone. The light power compensates for losses through the light fiber, two balloons, and tissue wall and may be balanced to avoid heat buildup during therapy.

In some embodiments, the apparatus 100 may provide a therapy utilizing multiple aqueous drugs with different methods of action. One drug may be delivered first and functionalized with the light fibers while the vessel is propped open, and subsequently another drug with antiproliferation capabilities may be delivered and not functionalized with the light fibers, and yet another drug with anti-inflammatory properties may be subsequently delivered providing a valuable combination of beneficial drugs without compromising one for the other.

Additionally, therapeutic agents useful with the device of the present disclosure include any one of or a combination of several agents which are gas, liquid, suspensions, emulsions, or solids, which may be delivered or collected from the vessel for therapeutic or diagnostic purposes. Therapeutic agents may include biologically active substances, or substances capable of eliciting a biological response, including, but not limited to endogenous substances (growth factors or cytokines, including, but not limited to basic fibroblast growth factor, acidic fibroblast growth factor, vascular endothelial growth factor, angiogenic factors, microRNA), viral vectors, DNA capable of expressing proteins, sustained release polymers, and unmodified or modified cells. Therapeutic agents may include angiogenic agents which induce the formation of new blood vessels. Therapeutic agents may also include anti-stenosis or anti-restenosis agents which are used to treat the narrowing of blood vessel walls. Therapeutic agents may include light-activated agents such as light-activated anti-stenosis or light-activated anti-restenosis agents that may be used to treat the narrowing of blood vessel walls.

Accordingly, apparatus 100 is multifunctional, providing drug delivery control in open and closed positions, and propping open a vessel wall forming a shape during drug functionalizing with a light source of a specific wavelength outside of the ultraviolet (UV) range (10 nm to 400 nm).

Another embodiment of this disclosure includes an exemplary method of tissue restoration in a blood vessel of a subject. The method may include providing a catheter into the blood vessel. In some embodiments, the catheter may include the features of apparatus 100 described above. For example, the catheter may include a catheter shaft (e.g. catheter shaft 104) extending from a proximal end (e.g. proximal end 106) to a distal tip (e.g. distal tip 110). A first distal balloon (e.g. first distal balloon 120) may be positioned on a translucent distal segment (e.g. distal segment 130) of the catheter shaft proximal to the distal tip, the first distal balloon in fluid communication with a drug source via a first lumen (e.g. first distal balloon inflation lumen 150). The first distal balloon may include a translucent material and be positioned inside of an concentric with a second distal balloon (e.g. second distal balloon 122), a plurality of longitudinal channels (e.g. longitudinal channels 124) recessed from a plurality of outermost radial surfaces (e.g. outermost radial surfaces 127) of the first distal balloon, a plurality of circumferential channels (e.g. circumferential fluid channels 126) recessed from the outermost radial surfaces of the first distal balloon. The second distal balloon (e.g. second distal balloon 122) may be in fluid communication with a second lumen (e.g. second distal balloon inflation lumen 154) separate from the first lumen. The catheter may further include a first light fiber (e.g. light fiber 140) and a second light fiber (e.g. light fiber 142) each positioned in the catheter shaft and extending through the translucent distal segment.

The method may further include supplying a drug from the drug source to the first distal balloon, delivering the drug to the treatment area through the slitted apertures (e.g. slitted apertures 198), activating the first light fiber and the second light fiber, thereby providing light transmission through the distal segment, the first distal balloon, and the second distal balloon to activate the drug in the treatment area. The light transmission to the treatment area may activate the Natural Vascular Scaffolding (NVS), which may be activated by light. The expansion of the first distal balloon may shape the treatment area (e.g. vessel) as desired.

The method may further include gradually filling the drug into a volume of the longitudinal channels and circumferential channels between an inside surface of the second distal balloon and an outside surface of the first distal balloon, and expanding the second distal balloon, thereby moving the slitted apertures away from the outermost radial surfaces of the first distal balloon.

Accordingly, the apparatus and methods described herein provide the delivery of NVS to a treatment area (e.g. a vessel) and provide restoration to that treatment area using the apparatus or according to the methods described above. The apparatus and method described above provide concurrently treating the vessel with one or more drugs (e.g. with Paclitaxel and NVS) with minimal loss to other vessels, scaffolding and casting the vessel, and light activation of the one or more drugs delivered to the treatment area. These advantages can be accomplished utilizing the apparatus and methods described herein.

According to embodiments of the present disclosure, NVS may include dimeric naphthalmides as described in U.S. Pat. No. 6,410,505 B2, and U.S. Provisional Patent Application No. 62/785,477. For example, a dimeric naphthalimide compound, 2,2'-((ethane-1,2-diylbis(oxy))bis(ethane-2,1-diyl))bis(6-((2-(2-(2-aminoethoxy)ethoxy)ethyl) amino)-1H-benzo[de]isoquinoline-1,3(2H)-dione), also known as 10-8-10 dimer, 6-[2-[2-(2-aminoethoxy)ethoxy] ethylamino]-2-[2-[2-[2-[6-[2-[2-(2-aminoethoxy)ethoxy] ethylamino]-1,3-dioxobenzo[de]isoquinolin-2-yl]ethoxy] ethoxy]ethyl]benzo[de]isoquinoline-1,3-dione; 2,2'-[1,2-ethanediylbix(oxy-2,1-ethanediyl)]bis[6-({2-[2-(2-aminoethoxy)ethoxy]ethyl}amino)-1H-benzo[de] isoquinoline-1,3(2H)-dione]; and 1H-benz[de]isoquinoline-1,3(2H)-dione, 2,2'-[1,2-ethanediylbis(oxy-2,1-ethanediyl)] bis[6-[[2-[2-(2-aminoethoxy)ethoxy]ethyl]amino]-(9Cl), and herein referred to as Compound of Formula (I), has been disclosed. Id.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented as hardware alone. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure (e.g., slitted apertures, apertures, perforations may be used interchangeably maintaining the true scope of the embodiments)

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. An apparatus comprising
   a catheter shaft extending from a proximal end to a distal tip;
   a first distal balloon positioned on a translucent distal segment of the catheter shaft proximal to the distal tip and positioned inside of and concentric with a second distal balloon, the first distal balloon in fluid communication with a drug source via a first lumen, the first distal balloon comprising:
   a translucent material;
   a plurality of longitudinal channels recessed from a plurality of outermost radial surfaces of the first distal balloon;
   a plurality of circumferential channels recessed from the outermost radial surfaces of the first distal balloon;
   the second distal balloon in fluid communication with a second lumen separate from the first lumen; and
   a first light fiber and a second light fiber each positioned in the catheter shaft and extending through the translucent distal segment.

2. The apparatus of claim 1, wherein the second distal balloon comprises a plurality of slitted apertures radially aligned with the outermost radial surfaces of the first distal balloon, the slitted apertures selectively communicate a drug from the first distal balloon to a treatment area of a subject.

3. The apparatus of claim 2, wherein the slitted apertures are positioned away from the longitudinal channels and the circumferential channels of the first distal balloon.

4. The apparatus of claim 2, wherein the slitted apertures of the second distal balloon remain in contact with the outermost radial surfaces of the first distal balloon, sealing the slitted apertures closed during inflation and deflation of the first distal balloon.

5. The apparatus of claim 2, wherein during inflation of the second distal balloon, the drug fills between an inside surface of the second distal balloon and an outside surface of the first distal balloon, gradually filling the longitudinal channels and circumferential channels.

6. The apparatus of claim 5, wherein a pressure of the drug between the inside surface of the second distal balloon and the outside surface of the first distal balloon increases and inflates the second distal balloon, the increased pressure forces edges of the slitted apertures to open apart thereby reducing the pressure.

7. The apparatus of claim 2, wherein inflation of the second distal balloon moves the slitted apertures away from the outermost radial surfaces of the first distal balloon allowing the slitted apertures to open and permit fluid flow to the treatment area.

8. The apparatus of claim 1 wherein the distal segment, the first distal balloon, and the second distal balloon are at least partially transparent.

9. The apparatus of claim 1 wherein the first light fiber and the second light fiber provide light activation through the distal segment, the first distal balloon, and the second distal balloon.

10. The apparatus of claim 1 wherein the longitudinal channels and circumferential channels are non-deformable and provide uniform drug delivery through the second distal balloon.

11. The apparatus of claim 1 wherein the second distal balloon comprises material that is conformable to the morphology of the vessel wall.

12. A method of tissue restoration in a blood vessel of a subject comprising:
    providing a catheter into the blood vessel, the catheter comprising:
    a catheter shaft extending from a proximal end to a distal tip;
    a first distal balloon positioned on a translucent distal segment of the catheter shaft proximal to the distal tip and positioned inside of and concentric with a second distal balloon, the first distal balloon in fluid communication with a drug source via a first lumen, the first distal balloon comprising:
    a translucent material;
    a plurality of longitudinal channels recessed from a plurality of outermost radial surfaces of the first distal balloon;
    a plurality of circumferential channels recessed from the outermost radial surfaces of the first distal balloon;
    the second distal balloon in fluid communication with a second lumen separate from the first lumen, the second distal balloon comprises a plurality of slitted apertures radially aligned with the outermost radial surfaces of the first distal balloon, the slitted apertures selectively communicate a drug from the first distal balloon to a treatment area of a subject; and a first light fiber and a second light fiber each positioned in the catheter shaft and extending through the translucent distal segment;

supplying the drug from the drug source to the first distal balloon;

delivering the drug to the treatment area through the slitted apertures;

activating the first light fiber and the second light fiber thereby providing light transmission through the distal segment, the first distal balloon, and the second distal balloon to activate the drug in the treatment area.

13. The method of claim 12 further comprising:

gradually filling the drug into a volume of the longitudinal channels and circumferential channels between an inside surface of the second distal balloon and an outside surface of the first distal balloon;

expanding the second distal balloon, thereby moving the slitted apertures away from the outermost radial surfaces of the first distal balloon.

14. The method of claim 13, wherein a pressure of the drug between the inside surface of the second distal balloon and the outside surface of the first distal balloon increases and inflates the second distal balloon, the increased pressure forces edges of the slitted apertures to open apart thereby reducing the pressure.

15. The method of claim 12, wherein the slitted apertures are positioned away from the longitudinal channels and the circumferential channels of the first distal balloon.

16. The method of claim 12, further comprising contracting the second distal balloon as the drug is delivered through the slitted apertures.

17. The method of claim 16, wherein contracting the second distal balloon moves the second distal balloon into contact with the outermost radial surfaces of the first distal balloon and closes the slitted apertures, causing drug delivery to stop.

18. The method of claim 12, wherein the first light fiber and the second light fiber provide light activation through the distal segment, the first distal balloon, and the second distal balloon.

19. The method of claim 12, wherein the slitted apertures are positioned away from the longitudinal channels and the circumferential channels of the first distal balloon.

20. An apparatus comprising a catheter shaft extending from a proximal end to a distal tip;

a first distal balloon positioned on a translucent distal segment of the catheter shaft proximal to the distal tip and positioned inside of and concentric with a second distal balloon, the first distal balloon in fluid communication with a drug source via a first lumen, the first distal balloon comprising:

a translucent material;

a plurality of longitudinal channels recessed from a plurality of outermost radial surfaces of the first distal balloon;

a plurality of circumferential channels recessed from the outermost radial surfaces of the first distal balloon;

the second distal balloon in fluid communication with a second lumen separate from the first lumen; and a first light fiber and a second light fiber each positioned in the catheter shaft and extending through the translucent distal segment;

wherein the drug source is configured to provide at least one drug to the first distal balloon via the first lumen and during inflation of the second distal balloon, the at least one drug fills between an inside surface of the second distal balloon and an outside surface of the first distal balloon, and gradually fills the longitudinal channels and circumferential channels.

* * * * *